United States Patent
Sondreaal (10) Patent No.: US 9,763,819 B1
(45) Date of Patent: Sep. 19, 2017

(54) TAPERED SLEEVE

(71) Applicant: W. L. Gore & Associates, Inc., Newark, DE (US)

(72) Inventor: Matthew G. Sondreaal, Phoenix, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 490 days.

(21) Appl. No.: 14/183,303

(22) Filed: Feb. 18, 2014

Related U.S. Application Data (60) Provisional application No. 61/772,984, filed on Mar. 5, 2013.

(51) Int. Cl.
*A61F 2/962* (2013.01)
*A61F 2/07* (2013.01)
*A61F 2/958* (2013.01)

(52) U.S. Cl.
CPC ............... *A61F 2/962* (2013.01); *A61F 2/07* (2013.01); *A61F 2/958* (2013.01)

(58) Field of Classification Search
CPC .. A61F 2/962; A61F 2/966; A61F 2/97; A61F 2002/9665
See application file for complete search history.

(56) References Cited

U.S. PATENT DOCUMENTS

| | | | |
|---|---|---|---|
| 4,921,479 A * | 5/1990 | Grayzel | A61M 25/0668 604/160 |
| 5,755,769 A | 5/1998 | Richard et al. | |
| 6,019,787 A | 2/2000 | Richard et al. | |
| 6,352,561 B1 | 3/2002 | Leopold et al. | |
| 7,198,636 B2 | 4/2007 | Cully et al. | |
| 2009/0182411 A1* | 7/2009 | Irwin | A61F 2/966 623/1.12 |
| 2010/0331955 A1* | 12/2010 | Vrba | A61F 2/01 623/1.11 |
| 2011/0137401 A1* | 6/2011 | Dorn | A61F 2/95 623/1.12 |
| 2011/0137402 A1* | 6/2011 | Dorn | A61F 2/95 623/1.12 |
| 2011/0208292 A1* | 8/2011 | Von Oepen | A61F 2/97 623/1.23 |
| 2012/0120287 A1 | 5/2012 | Funamoto et al. | |
| 2012/0130473 A1* | 5/2012 | Norris | A61F 2/97 623/1.12 |
| 2012/0296412 A1* | 11/2012 | Paul | A61B 17/12109 623/1.12 |
| 2013/0158524 A1* | 6/2013 | Fargahi | A61F 2/97 606/1 |

(Continued)

FOREIGN PATENT DOCUMENTS

WO    WO 2010/063795    *    6/2010    ............... A61F 2/84

*Primary Examiner* — Sarah W Aleman (57) ABSTRACT

The present disclosure describes a sleeve comprising a conical frustum having first and second end profiles and a lumen there through for covering and constraining an expandable device, and assemblies comprising an expandable device and a sleeve having a frustoconical shape when the expandable device is at least partially expanded. The present disclosure further describes methods for deploying an expandable device in a patient comprising releasing a releasable seam disposed on a sleeve and everting the sleeve while retracting it from the expandable device.

20 Claims, 4 Drawing Sheets

(56) References Cited

U.S. PATENT DOCUMENTS

| | | | |
|---|---|---|---|
| 2013/0211493 A1* | 8/2013 | Wubbeling | A61F 2/95 623/1.11 |
| 2014/0130475 A1 | 5/2014 | Van Berkel et al. | |
| 2014/0135895 A1* | 5/2014 | Andress | A61F 2/97 623/1.12 |

* cited by examiner

TAPERED SLEEVE

FIELD

The present disclosure relates generally to the remote orientation and deployment of implantable medical devices and, more particularly, to implantable expandable devices surrounded by constraining sleeves.

BACKGROUND

Medical devices are frequently used to treat the anatomy of patients. Such devices can be permanently or semi-permanently implanted in the anatomy to provide treatment to the patient. Frequently, these devices, including stents, grafts, stent-grafts, filters, valves, occluders, markers, mapping devices, therapeutic agent delivery devices, prostheses, pumps, bandages, and other endoluminal and implantable devices, are inserted into the body at an insertion point and delivered to a treatment site using a catheter. Common types of expandable devices include stents and stent-grafts.

Expandable devices such as stents or stent-grafts are used in a variety of places in the human body to repair aneurysms and to support various anatomical lumens, such as blood vessels, respiratory ducts, gastrointestinal ducts, and the like. Expandable devices can have a reduced diameter when in a collapsed configuration, and can be designed to spontaneously dilate (i.e., elastically recover), or be balloon-expanded, from their collapse configuration, through one or more intermediate configurations, up to a maximum functional configuration. Expandable devices can be constrained in the collapsed configuration with a sleeve to facilitate transport to the treatment site.

The endoluminal delivery and deployment of expandable devices pose potential issues. First, the expandable device itself must be radially compacted to a suitable delivery configuration to allow insertion into the vasculature, constrained and mounted onto a delivery device such as a catheter. Subsequently, the constraint must be removed in order to allow the expandable device to expand or be expanded to its functional configuration and achieve the desired therapeutic outcome. A variety of ways of constraining and deploying an expandable device are known in the art. For example, an expandable device can be constrained by one or more sleeves with deployment comprising the removal of the one or more sleeves.

As such, there is an ongoing need to improve the endoluminal delivery and deployment of expandable devices such as stents and stent-grafts. New devices, assemblies and methods of deployment that can improve the use of sleeve-constrained expandable implants would be useful and desirable.

BRIEF DESCRIPTION OF THE DRAWINGS

The accompanying drawings are included to provide a further understanding of the disclosure. The drawings incorporated in and constituting a part of this specification illustrate embodiments of the disclosure, and together with the description, serve to explain the principles of the disclosure, wherein like numerals denote like elements and wherein.

DETAILED DESCRIPTION OF THE ILLUSTRATED EMBODIMENTS

Persons skilled in the art will readily appreciate that various aspects of the present disclosure can be realized by any number of methods and systems configured to perform the intended functions. Stated differently, other methods and systems can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting.

With that said, and as will be described in more detail herein, various embodiments of the present disclosure generally comprise sleeves comprising a conical frustum usable for constraining expandable devices, assemblies comprising an expandable device and a sleeve having a frustoconical shape when the expandable device is in an intermediate configuration, and methods for deploying an expandable device in a patient comprising the eversion and retraction of a frustoconical-shaped sleeve from an expandable device.

As used herein, "proximal" indicates a position closer to the heart of the patient, or to a portion of a device that, when implanted, is closer to the heart of the patient than another portion of the device. "Distal" indicates a position farther from the heart of the patient, or to a portion of a device that, when implanted, is farther from the heart of the patient than another portion of the device. Implanted devices having tubular or rod-like shape comprise a distal end, a distal portion, a medial portion, a proximal portion, and a proximal end moving from the end farthest from the heart to the end closest to the heart.

With further regard to the terms proximal and distal, and because the present disclosure is not limited to peripheral and/or central approaches, this disclosure should not be narrowly construed with respect to these terms. Rather, the devices and method described herein can be altered and/or adjusted relative to the anatomy of a patient.

An "expandable device" can include, for example, any device suitable for delivery to the treatment site at a delivery diameter and capable of dilation from the diameter of the delivery profile, through a range of intermediary diameters, up to a maximal, pre-determined functional diameter. Such expandable devices can include endoluminal prostheses such as stents, grafts and stent-grafts.

As used herein, an "assembly" can include, for example, a combination of an expandable device, such as a stent or stent-graft, a delivery device, such as a catheter, and other related accessories, components, and devices.

As used herein, a "sleeve" can include any enclosure constraining an expandable device. In various embodiments, a sleeve can comprise a sheet of material wrapped around an expandable device in a collapsed, intermediate, or treatment configuration.

As used herein, the term "constrain" means: (i) to limit expansion, occurring either through self-expansion or assisted expansion, of the diameter of an expandable implant; or (ii) to cover or surround, but not otherwise restrain, an expandable implant such as for storage or biocompatibility reasons and/or to provide protection to the expandable implant and/or the vasculature.

As used herein, "deployment" refers to the actuation of a device at a treatment site, such as for example, the release and/or removal of a sleeve from a self-expanding device to allow the device to expand. The deployment process can be in stages, such as for example, a first stage comprising the release of a sleeve to a configuration suitable to constrain the expandable device only to an intermediate configuration, and a second stage comprising the removal of the sleeve altogether from the device.

As used herein, "conical frustum" means a portion of a hollow cone that lies between two parallel planes cutting it, or in other words, a truncated cone. As used herein, "frustoconical" means having the shape of a frustum of a cone.

As used herein, "eversion" means a process whereby a structure is turned inside-out. As used herein, "evert" means to turn something inside-out. An "everted" structure is a structure that has been everted, (i.e., turned inside-out).

Sleeves in accordance with the present disclosure can comprise a conical frustum that constrains an expandable device in an intermediate configuration. In various embodiments, a sleeve can be any other shape suitable for constraining an expandable device in a collapsed configuration. In various embodiments, a sleeve can change shape from a first shape that constrains an expandable device in a collapsed configuration, to a second shape that constrains the expandable device to an intermediate or fully expanded configuration. In various embodiments, a sleeve can be entirely removed from an expandable device by everting the sleeve while retracting it from the expandable device.

Figure 1A:
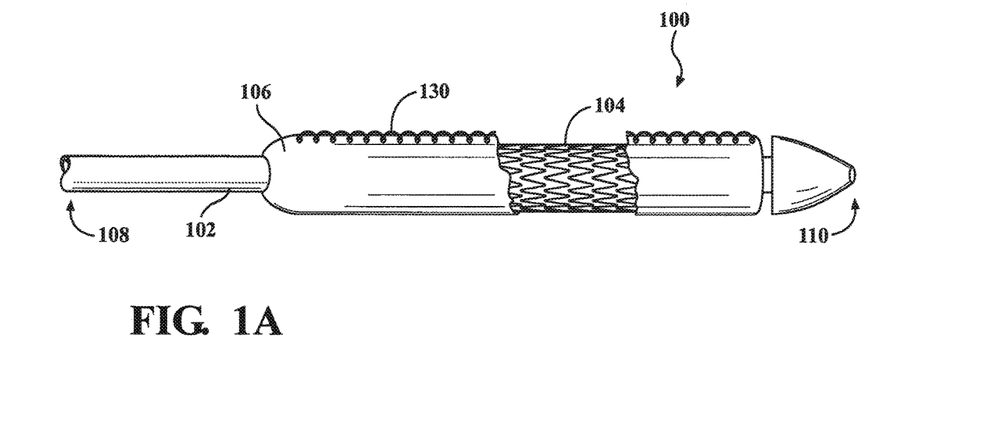
FIG. 1A illustrates a partial cutaway side view of an embodiment of an assembly comprising an expandable device constrained in a collapsed configuration in accordance with the present disclosure.

With reference now to FIG. 1A, an assembly 100 in accordance with the present disclosure is illustrated in a partial cutaway side view. Assembly 100 comprises an expandable device 104 (viewable within the partial cutaway for discussion purposes), and at least one sleeve 106. As illustrated in FIG. 1A, the sleeve 106 circumferentially surrounds the expandable device 104, and constrains it in a collapsed configuration in which the diameter is less than the diameter of any intermediate configuration, which is less than the diameter of a fully expanded, treatment configuration. In various embodiments, the sleeve 106 can constrain an expandable device 104 to any intermediate diameter between the fully expanded diameter and the fully collapsed diameter. At least one coupling member 130 can coordinate with rows of openings disposed on the sleeve 106 to secure the sleeve 106 around the expandable device 104.

In various embodiments, the coupling member 130 can comprise a woven fiber or a monofilament fiber. Any type of string, cord, thread, fiber, or wire capable of constraining a sleeve around an expandable device is within the scope of the present disclosure. For example, the coupling member can comprise expanded polytetrafluoroethylene (ePTFE), ePTFE fiber such as (KORETEK®), sutures of polyethers such as polyethylene terephthalate (DACRON® or MYLAR®) or polyacrylamides such as KEVLAR®. The coupling member 130 may comprise a metal wire made from nitinol, stainless steel, or gold.

In various embodiments, the assembly 100 can include a catheter 102 having a distal end 108 and a proximal end 110. The expandable device 104 can be constrained in a collapsed configuration by sleeve 106 and mounted near the proximal end 110 of the catheter 102. The assembly 100 also has proximal and distal ends that correspond to those of the catheter 102.

In various embodiments, expandable device 104 comprises a stent-graft. Stent-grafts are designed to expand from a collapsed delivery diameter, through a range of intermediary diameters, up to a maximum, often pre-determined functional diameter, and generally comprise one or more stents and one or more graft members disposed over and/or under the stent.

In various embodiments, the expandable device 104 can comprise a stent. A stent can include, for example, a plurality of stent rings, cut tubes, wound wires (or ribbons) or flat patterned sheets rolled into a tubular form. Stent rings can be operatively coupled to one another with a wire. Stent components can be formed from metallic, polymeric or natural materials and can comprise conventional medical grade materials such as for example nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as iron alloys, stainless steels, cobalt-chromium alloys, nitinol, and the like; and biologically derived materials such as bovine arteries/veins, pericardium and collagen. Stent components can also comprise bioresorbable organic materials such as poly(amino acids), poly(anhydrides), poly(caprolactones), poly(lactic/glycolic acid) polymers, poly(hydroxybutyrates) and poly(orthoesters).

In various embodiments, expandable device 104 can be self-expanding. Such devices dilate from a radially collapsed configuration to a radially expanded configuration when unconstrained.

In various embodiments, expandable device 104 can be balloon-expandable with the assistance of a secondary device such as, for example, a balloon catheter or spring mechanism.

In various embodiments, the expandable device 104 can further comprise at least one graft member. The graft member can comprise, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof. Other embodiments for graft material can include high strength polymer fibers such as ultra-high molecular weight polyethylene fibers (e.g., Spectra®, Dyneema Purity®, etc.) or aramid fibers (e.g., Technora®, etc.).

Figure 1B:
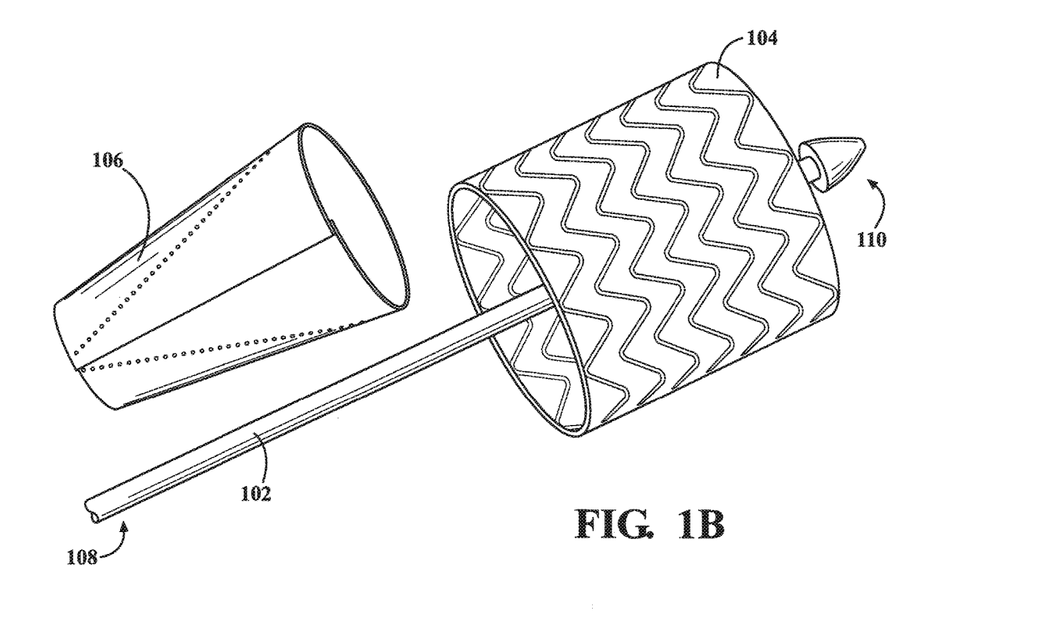
FIG. 1B illustrates side views of embodiments of an expanded device and a sleeve in accordance with the present disclosure.

As illustrated in FIG. 1B, expandable device 104, unconstrained by sleeve 106, can comprise a radially expanded configuration suitable for implant in the treatment area of a patient's vasculature. In the expanded configuration, the diameter of expandable device 104 can be approximately the same as the vessel to be repaired, or slightly larger than the vessel to be treated to provide a traction fit within the vessel. Prior to expansion of the expandable device 104 to the expanded configuration engaged with the vasculature, sleeve 106 may have constrained the expandable device 104 in an intermediate configuration. In various embodiments, the sleeve 106 can comprise a first end profile, a second end profile and a lumen extending between the end profiles, wherein the first end profile and second end profile are different. In various embodiments, the end profiles can be planar, and parallel. In some embodiments, planar end profiles need not be parallel. In various embodiments, the sleeve 106 can be frustoconical, with opposing end portions having planar circular perimeters parallel to each other. In various embodiments, either or both circular end portions can be non-planar.

Figure 2:
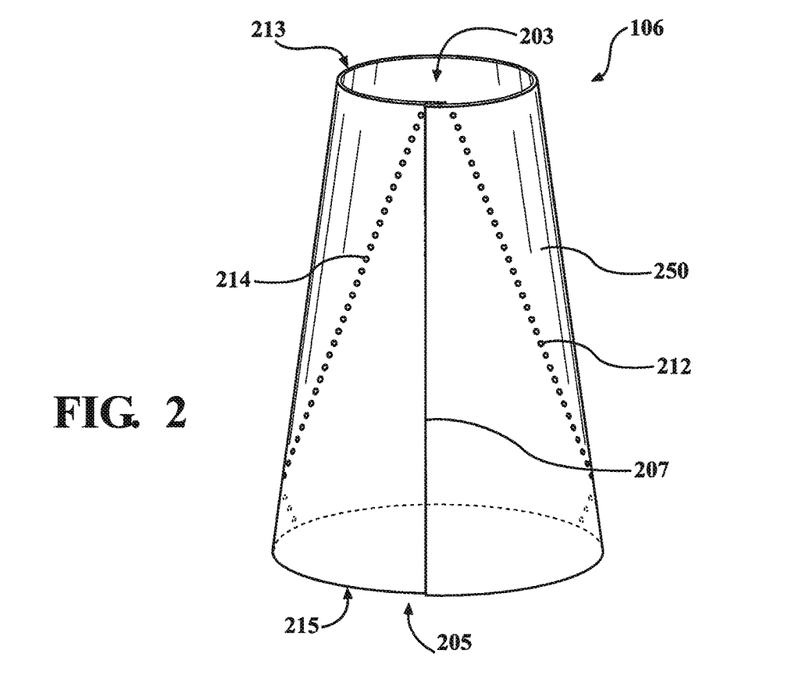
FIG. 2 illustrates a perspective view of an embodiment of a sleeve in accordance with the present disclosure.

Referring now to FIG. 2, sleeve 106 comprises a conical frustum having a first end profile 203 with first end profile perimeter 213, and a second end profile 205 with second end profile perimeter 215. In various embodiments, each of first end profile perimeter 213 and second end profile perimeter 215 are substantially circular, though they may have non-circular shapes in other embodiments. In various embodiments, first end profile 203 and second end profile 205 can be substantially planar and parallel to each other. In various embodiments, the difference in size between the first end profile 203 and the second end profile 205 can be about twice the wall thickness of the sleeve 106, or greater, as discussed below. In some embodiments, the difference in size need only be the difference required for the sleeve 106 to be everted.

Sleeve 106 further comprises a first seam 207 disposed between first end profile 203 and second end profile 205, though in other embodiments, sleeve 106 can be formed without such a seam. For example, sleeve 106 can be made by wrapping tape around a frustoconical mandrel and thermally bonding the windings into a sleeve, optionally leaving an end of the tape extending from the sleeve for attachment to one or more pull members (discussed below). In various other embodiments, sleeve 106 can be made by an extrusion process, or by stretching a cylindrical sleeve over a frustoconical mandrel into a tapered, frustoconical shape. Sleeve 106 can be formed from a sheet of material 250 wrapped into a frustoconical shape and joined along first seam 207. In various embodiments, first seam 207 can be perpendicular to both first end profile 203 and second end profile 205. By wrapping a sheet of material, sleeve 106 includes a lumen that extends through the conical frustum and connects the first end profile 203 and the second end profile 205. In various embodiments, first seam 207 can be releasable (i.e., it can be opened) or permanent.

In various embodiments, a sheet of material 250 of any particular thickness can be wrapped to form a frustoconical sleeve 106, wherein the difference in the diameter of second end profile 205 and the diameter of the first end profile 203 is equal to, or greater than, twice the thickness of the sheet of material 250.

In some embodiments, sleeve 106 further comprises a first row of openings 212 and a second row of openings 214 that can be coupled together into a releasable second seam with a coupling member (e.g., coupling member 130 in FIG. 1A) to reduce the overall size of sleeve 106, possibly change its shape, and constrain an expandable device within sleeve 106 to a collapsed delivery configuration.

In various embodiments, sleeve 106 can comprise materials similar to those used to form graft members. A sleeve can be made of any suitable material, including for example, a fluoropolymer such as ePTFE. Alternatively, or in combination with a fluoropolymer, the sleeve can be formed of biocompatible materials, such as polymers, which can include fillers such as metals, carbon fibers, Dacron, glass fibers or ceramics. Such polymers can include olefin polymers, polyethylene, polypropylene, polyvinyl chloride, polytetrafluoroethylene which is not expanded, fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalates, polypropylenes, polyethylenes, polyurethanes, polyolefins, polyvinyls, polymethylacetates, polyamides, naphthalane dicarboxylene derivatives, and natural silk can be included in the sleeve.

Figure 3:
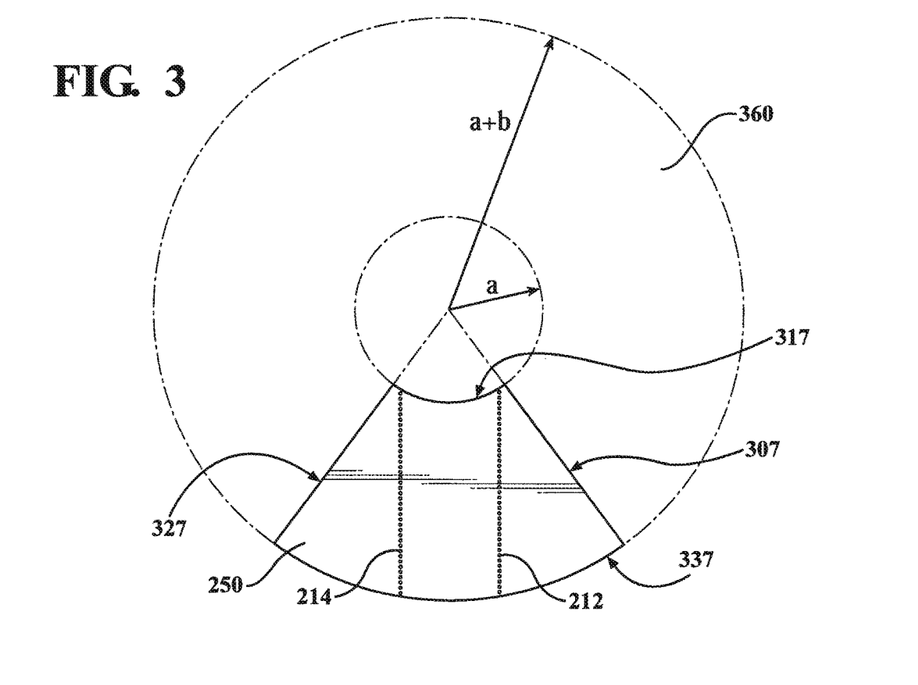
FIG. 3 illustrates an unwrapped sheet of material usable to form an embodiment of a sleeve in accordance with the present disclosure.

Referring now to FIG. 3, an unwrapped sheet of material 250 for forming a sleeve, such as for example sleeve 106, is illustrated. In various embodiments, sheet of material 250 can comprise the minor portion of an annulus 360 having minor arc of radius a and major arc of radius (a+b). First straight end 307 and second straight end 327 can be brought together to form first seam 207 (FIG. 2). In this way, the sheet of material 250 can be wrapped around an expandable device to constrain the expandable device in an intermediate configuration. In this way, the first seam 207 (FIG. 2), formed by joining the two opposite straight ends of the minor portion of the annulus, can have length approximately equal to b.

With continued reference to FIG. 3, sheet of material 250 can further comprise a first row of openings 212 and a second row of openings 214. The rows of openings can be linear and parallel to each other. In various embodiments, the first row of openings 212 can begin at a point where first straight end 307 meets the minor arced edge 317. Similarly, the second row of openings 214 can begin at a point where second straight end 327 meets the minor arced edge 317. Both rows of openings can extend out to the major arced edge 337 of the annulus portion as illustrated. As discussed, first row of openings 212 and second row of openings 214 can be joined into a releasable second seam with a coupling member threaded or woven through the openings. A coupling member can be of sufficient length to form a remote pull line used for tensioning and deployment of an expandable device constrained by a sleeve. When an expandable device is at the treatment site of the patient, the coupling member can be disengaged from the sleeve from outside of the body of the patient, which allows the sleeve to open along the releasable seam and the expandable device to expand or be available for assisted expansion.

Figure 4A:
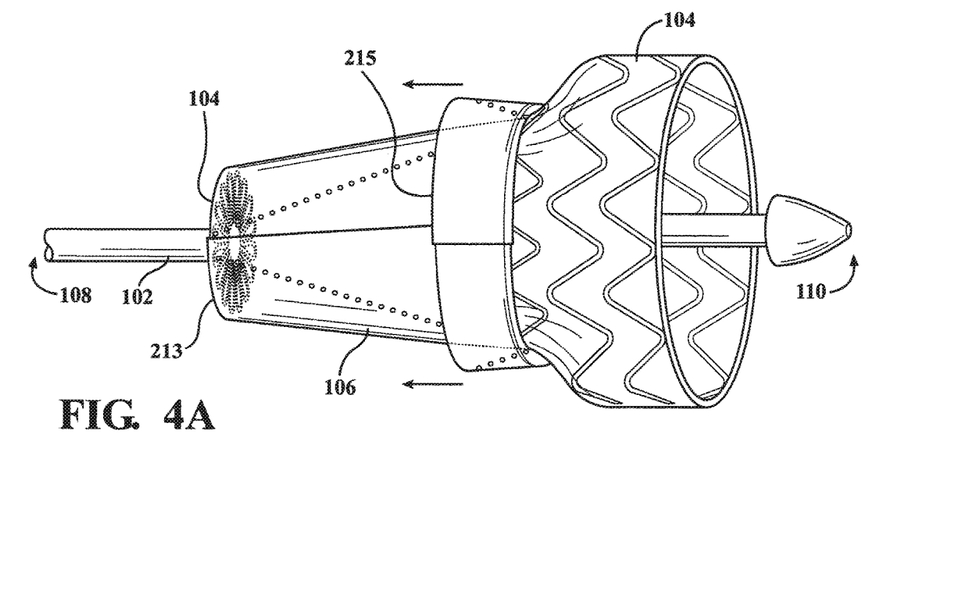
FIGS. 4A, 4B and 4C illustrate side views of an embodiment of an expandable device being deployed in accordance with the present disclosure.
Figure 4B:
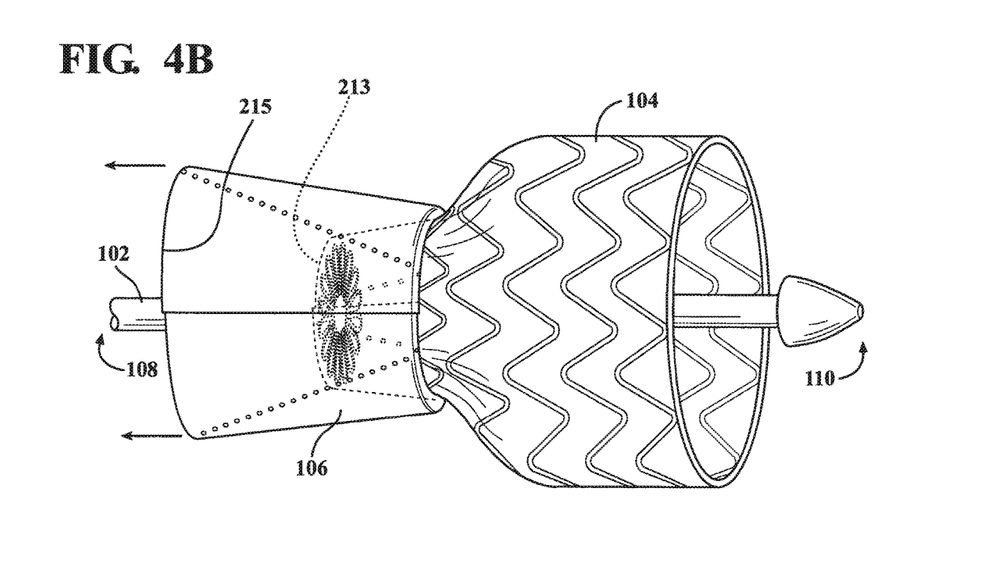
Figure 4C:
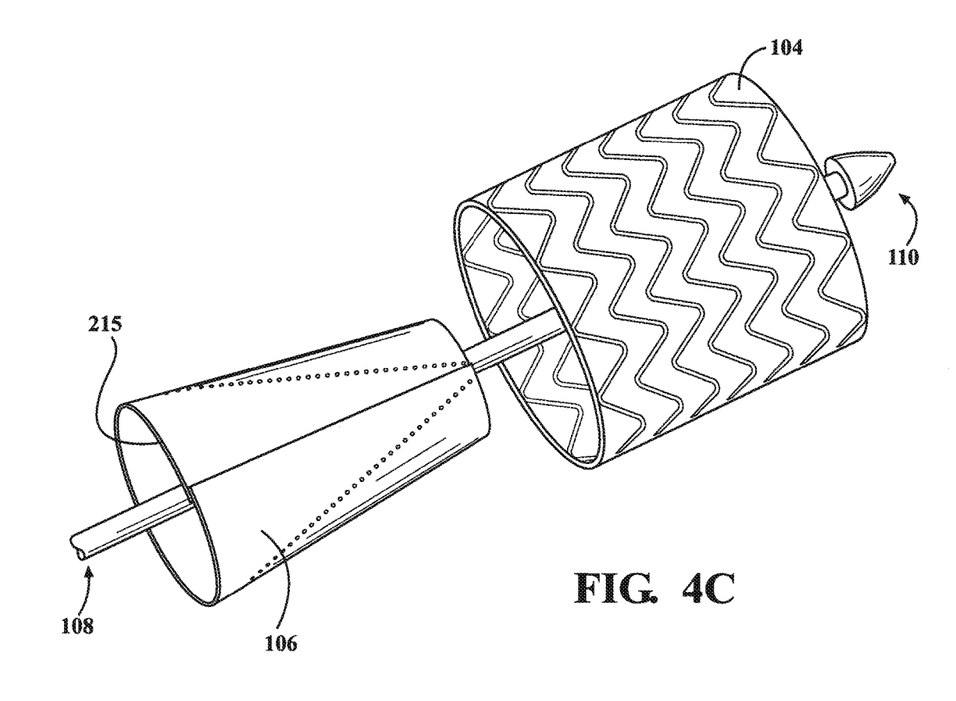

FIGS. 4A, 4B and 4C illustrate an embodiment of a method of deploying an expandable device in a patient in accordance with the present disclosure. In various embodiments, deployment of an expandable device can comprise at least two stages. For example, a first stage can comprise the opening of a releasable second seam on a sleeve, allowing an expandable device constrained therein to self-expand, or be available for expansion, from a collapsed delivery configuration to an intermediate configuration. In various embodiments, the tensioning and removal of a coupling member from the sleeve can operate to open the releasable second seam. The sleeve can comprise a conical frustum when the expandable device is in an intermediate configuration. For example, after tensioning and removal of a coupling member, the sleeve can comprise a conical frustum having a smaller first end profile at the distal end of the sleeve and a larger second end profile at the proximal end of the sleeve. In various embodiments, the sleeve, prior to the opening of the releasable second seam, can begin in a cylindrical shape, or in any other shape suitable to constrain the expandable device in a collapsed delivery configuration.

In various embodiments, the first stage of deployment can comprise the release of a primary sleeve that coaxially surrounds both an inner secondary sleeve and an expandable device. In this way, release of the primary sleeve allows the expandable device to self-expand, or to be available for expansion, to an intermediate configuration still constrained by a secondary sleeve comprising a conical frustum or other shape.

In various embodiments of a method for deploying an expandable device in a patient, a second stage can include retracting and removing a sleeve from the expandable device through eversion. For example, a frustoconical-shaped sleeve can be everted and removed from an expandable device by retracting the larger second end profile of the sleeve in a distal direction over the tapered body of the sleeve toward and over the smaller first end profile. In various embodiments, one or more remote pull lines can be tethered to the larger end profile of the sleeve to assist in a controlled and even retraction of the sleeve. For example, several pull lines can be tethered symmetrically around the second end profile. In various embodiments, the tethered pull line or pull lines can be formed as an integral portion of the larger end profile of the sleeve, such as through extension of a reinforcing fiber that circumscribes the larger end profile. These and other configurations for the larger end profile of the sleeve can help maintain strength and a low delivery profile for the sleeve.

By retraction of the larger end profile of the sleeve, the sleeve is everted as the larger second end profile is pulled over and past the smaller first end profile. By continued retraction, the sleeve is completely everted and removed from the expandable device, with the first smaller end profile of the sleeve departing from the distal end of the expandable device at the completion of the eversion process. As the sleeve is everted in this manner, the expandable device expands, or becomes available for expansion, from an intermediate configuration to a fully expanded treatment configuration. Optionally, once the sleeve is everted and removed, any unexpanded portions of the expandable device may be optionally expanded.

With reference now to FIG. 4A, sleeve 106 comprising a conical frustum is everted and retracted from expandable device 104 by pulling the larger second end profile perimeter 215 in the distal direction over the tapered body of sleeve 106 toward the smaller first end profile perimeter 213, as shown by the directional arrows. During the eversion, the larger second end profile perimeter 215 will circumferentially surround the tapered body of the sleeve as the larger second end profile perimeter 215 is retracted. With the expandable device in an intermediate configuration, rather that in a collapsed delivery configuration, the radial force from the expandable device 104 on the sleeve 106 has less impact on the eversion process. In this way, a sleeve comprising a conical frustum can be everted and pulled off an expandable device by retraction in the distal direction. As is shown in FIGS. 1B, 2, 3, 4A, 4B, and 4C, in multiple embodiments of the present invention the sleeve 106 may be configured to form a frustoconical shape along its entire length from end to end.

Referring now to FIG. 4B, further retraction of the second end profile perimeter 215 over and beyond the first end profile perimeter 213 in a distal direction continues to evert the sleeve 106 to ultimately free it from the expandable device 104.

Referring now to FIG. 4C, continued retraction of the second end profile perimeter 215 in a distal direction ultimately frees the sleeve 106 from the expandable device 104. In this way, the sleeve 106 is turned inside-out when fully separated from the expandable device 104.

It will be apparent to those skilled in the art that various modifications and variations can be made in the present disclosure without departing from the spirit and scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A sleeve for covering and constraining an expandable device for endoluminal delivery, the sleeve being transitionable between a delivery configuration and a deployment configuration, the sleeve comprising a first end profile, a second end profile, a length extending between the end profiles, and a lumen extending between the end profiles;
wherein in the delivery configuration the sleeve includes a seam formed between a first portion of the sleeve and a second portion of the sleeve along which the first and second portions extend, and wherein in the deployment configuration the seam is released and the sleeve forms a conical frustum such that the first and second portions diverge from one another as they extend between the first and second end profiles.

2. The sleeve of claim 1, comprising an annulus having a minor portion, a major portion, a first straight end, and a second separate straight end, the first and second separate straight ends extending between the minor and major portions and being joined together to form a second seam that maintains the sleeve in the conical frustum form in the deployment configuration.

3. The sleeve of claim 2 wherein the sleeve is formed of an annular shaped sheet of material.

4. The sleeve of claim 1 wherein the first portion of the sleeve includes a first row of openings and wherein the second portion of the sleeve includes a second row of openings, the first and second rows of openings being joined together with a coupling member to form the seam in the delivery configuration.

5. The sleeve of claim 1, wherein the sleeve comprises ePTFE.

6. An assembly comprising:
an expandable device; and
a sheet having a length and being transitionable between a delivery configuration and a deployment configuration, the sheet releasably constraining the expandable device for endoluminal delivery, the sheet having a first coupling portion and a second coupling portion;
wherein in the delivery configuration the first and second coupling portions are joined together to form a seam that extends along the length of the sheet, and wherein in the deployment configuration the seam is released such that the first and second coupling portions are separated by a portion of the sheet that tapers such that the sheet adopts a frustoconical shape along the length of the sheet.

7. The assembly of claim 6, wherein the sleeve comprises a sheet of material having two separate, non-parallel straight ends joined together to form a second seam that maintains the sheet in the frustoconical shape in the deployment configuration.

8. The assembly of claim 7, wherein the sheet of material comprises an annulus having a minor portion and a major portion, the two separate, non-parallel straight ends extending between the minor and major portions, the sheet of material being wrapped around at least a portion of the expandable device.

9. The assembly of claim 6, wherein the first coupling portion is formed as first row of openings and wherein the second coupling portion is formed as a second row of openings, the first and second rows of openings being joined together with a coupling member to form the seam.

10. The assembly of claim 6, wherein the sleeve comprises ePTFE.

11. A method for deploying an expandable device in a patient comprising:
   providing an assembly that comprises:
      an expandable device; and
      a sleeve surrounding at least a portion of the expandable device, the sleeve being transitionable between a delivery configuration and a deployment configuration, the sleeve having a first end profile, a second end profile, a length extending between the end profiles, a lumen extending between the end profiles, a first row of openings, and a second row of openings, the first and second row of openings extending along the length;
   moving the assembly in the patient to a treatment site with the sleeve in the delivery configuration such that the first and second rows of openings are joined together to form a seam that extends along the length of the sleeve;
   releasing the seam such that the first and second rows of openings separate and diverge from one another as they extend between the first and second end profiles such that the sleeve adopts a frustoconical shape; and
   retracting the sleeve from the expandable device.

12. The method of claim 11, wherein the first and second rows of openings are joined together with a coupling member to form the seam, and wherein removal of the coupling member from the first and second rows of openings releases the seam such that the first and second rows of openings separate and diverge from one another.

13. The method of claim 11, wherein the expandable device comprises a stent graft that is at least one of a self-expanding stent graft and a balloon-expandable stent graft.

14. The method of claim 11, wherein the expandable device further comprises one or more unexpanded portions, the method further comprising expanding the one or more unexpanded portions of the expandable device.

15. The method of claim 11, wherein the sleeve is everted as it is retracted from the expandable device.

16. A medical device comprising:
   a sleeve for covering an expandable device for endoluminal delivery, the sleeve being transitionable between a delivery configuration and a deployment configuration, the sleeve comprising a first end profile, a second end profile, a first coupling portion, and a second coupling portion;
   wherein in the delivery configuration the first and second coupling portions are joined together to form a seam that extends between the first and second end profiles, and wherein in the deployment configuration the seam is released such that the first and second coupling portions are separated by portion of the sleeve that tapers between the first and second end profiles.

17. The medical device of claim 16, wherein the first and second coupling portions are nonparallel in the deployment configuration.

18. The medical device of claim 17, wherein the first and second coupling portions are substantially parallel to one another in the delivery configuration.

19. The medical device of claim 16, wherein the portion of the sleeve that tapers is tapered such that, in the deployment configuration, the first and second coupling portions are more proximate one another at the first end profile than they are at the second end profile.

20. The medical device of claim 16, wherein the first coupling portion is formed as first row of openings and wherein the second coupling portion is formed as a second row of openings, the first and second rows of openings being joined together with a coupling member to form the seam.

* * * * *